United States Patent
Soh

(10) Patent No.: US 10,857,086 B2
(45) Date of Patent: *Dec. 8, 2020

(54) HAIR CONDITIONING COMPOSITION COMPRISING CYCLIC COMPOUNDS AND COMPOUNDS HAVING AT LEAST THREE HEAD GROUPS

(71) Applicant: The Procter & Gamble Company, Cincinnati, OH (US)

(72) Inventor: Mui Siang Soh, Singapore (SG)

(73) Assignee: The Procter and Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/349,271

(22) Filed: Nov. 11, 2016

(65) Prior Publication Data

US 2017/0135927 A1    May 18, 2017

Related U.S. Application Data

(60) Provisional application No. 62/254,194, filed on Nov. 12, 2015.

(51) Int. Cl.

| | | |
|---|---|---|
| *A61K 8/67* | (2006.01) | |
| *A61K 8/31* | (2006.01) | |
| *A61K 8/368* | (2006.01) | |
| *A61K 8/37* | (2006.01) | |
| *A61K 8/41* | (2006.01) | |
| *A61K 8/49* | (2006.01) | |
| *A61K 8/63* | (2006.01) | |
| *A61K 8/899* | (2006.01) | |
| *A61Q 5/12* | (2006.01) | |
| *A61K 8/898* | (2006.01) | |

(52) U.S. Cl.
CPC .............. *A61K 8/675* (2013.01); *A61K 8/31* (2013.01); *A61K 8/368* (2013.01); *A61K 8/37* (2013.01); *A61K 8/375* (2013.01); *A61K 8/416* (2013.01); *A61K 8/494* (2013.01); *A61K 8/4926* (2013.01); *A61K 8/4953* (2013.01); *A61K 8/63* (2013.01); *A61K 8/898* (2013.01); *A61K 8/899* (2013.01); *A61Q 5/12* (2013.01)

(58) Field of Classification Search
None
See application file for complete search history.

(56) References Cited

U.S. PATENT DOCUMENTS

| | | |
|---|---|---|
| 6,569,414 B1 | 5/2003 | Bernecker et al. |
| 9,242,123 B2 | 1/2016 | Mahmud et al. |
| 9,549,885 B2 | 1/2017 | Aistrup et al. |
| 2005/0063934 A1 | 3/2005 | Baker |
| 2009/0074690 A1 | 3/2009 | Biganska |
| 2010/0120871 A1 | 5/2010 | Dawson, Jr. et al. |
| 2010/0260700 A1 | 10/2010 | Dop |
| 2015/0044156 A1 | 2/2015 | Schulze Zur Wiesche |
| 2015/0093347 A1 | 4/2015 | Uehara et al. |
| 2015/0093420 A1 | 4/2015 | Snyder et al. |

FOREIGN PATENT DOCUMENTS

| | | |
|---|---|---|
| JP | 2009067734 A | 4/2009 |
| JP | 2011195553 A | 10/2011 |
| JP | 5616607 B2 | 9/2014 |
| JP | 5933951 B2 | 5/2016 |
| WO | WO 00/64412 A | 11/2000 |
| WO | WO 01/01937 A1 | 1/2001 |
| WO | WO 2013/083349 A1 | 6/2013 |

OTHER PUBLICATIONS

PCT International Search Report and Written Opinion for PCT/US2016/06145 dated Feb. 7, 2017, 13 pages.

*Primary Examiner* — Bethany P Barham
*Assistant Examiner* — Barbara S Frazier
(74) *Attorney, Agent, or Firm* — Angela K. Haughey

(57) ABSTRACT

Disclosed is a hair conditioning composition comprising: a cationic surfactant; a high melting point fatty compound; a cyclic compound selected from the group consisting of a vitamin B3 compound, a xanthine compound, a salicylic acid ester, and mixtures thereof; a compound having at least three large head groups; and an aqueous carrier. The composition of the present invention provides improved hair manageability.

3 Claims, No Drawings

HAIR CONDITIONING COMPOSITION COMPRISING CYCLIC COMPOUNDS AND COMPOUNDS HAVING AT LEAST THREE HEAD GROUPS

FIELD OF THE INVENTION

The present invention relates to a hair conditioning composition comprising: a cationic surfactant; a high melting point fatty compound; a cyclic compound selected from the group consisting of a vitamin B3 compound, a xanthine compound, a salicylic acid ester, and mixtures thereof; a compound having at least three large head groups; and an aqueous carrier. The composition of the present invention provides improved hair manageability.

BACKGROUND OF THE INVENTION

A variety of approaches have been developed to condition the hair. A common method of providing conditioning benefit is through the use of conditioning agents such as cationic surfactants and polymers, high melting point fatty compounds, low melting point oils, silicone compounds, and mixtures thereof. Most of these conditioning agents are known to provide various conditioning benefits.

However, there is still a need for providing improved hair manageability, for example, improved hair alignment on dry hair after combing, reduced volume on dry hair (especially at the bottom side of hair) after combing, and/or curl-in hair tips after combing on dry hair. Additionally, there may exist a need for providing the above hair manageability, while not deteriorating other benefits, for example, at least one of the followings: improved spreadability; reduced sliminess on wet hair; and improved clean feel (i.e., reduced greasy/sticky feel) on dry hair; and free flowing (i.e., reduced clumpy hair) on dry hair. None of the existing art provides all of the advantages and benefits of the present invention.

SUMMARY OF THE INVENTION

The present invention is directed to a hair conditioning composition comprising by weight:
from about 1.0% to about 10% of a cationic surfactant;
from about 2.5% to about 30% of a high melting point fatty compound;
from about 0.2% to about 10% of a cyclic compound selected from the group consisting of a vitamin B3 compound, a xanthine compound, a salicylic acid ester, and mixtures thereof;
from about 0.1% to about 25% of a compound having at least three large head groups; and
an aqueous carrier.

The composition of the present invention provides improved hair manageability, for example, improved hair alignment on dry hair after combing, reduced volume on dry hair (especially at the bottom side of hair) after combing, and/or curl-in hair tips after combing on dry hair. The composition of the present invention may provide at least one of the followings: improved spreadability; reduced sliminess on wet hair; and improved clean feel (i.e., reduced greasy/sticky feel) on dry hair; and free flowing (i.e., reduced clumpy hair) on dry hair, while providing the above hair manageability.

Hair manageability may be achieved by containing conditioning agents at higher levels. However, such compositions often compromise other benefits, for example, at least one of the followings: improved spreadability; reduced sliminess on wet hair; and improved clean feel (i.e., reduced greasy/sticky feel) on dry hair; and free flowing (i.e., reduced clumpy hair) on dry hair. The composition of the present invention may meet such contradictional needs which are often compromised when providing hair manageability, for example, at least one of the followings: improved spreadability; reduced sliminess on wet hair; and improved clean feel (i.e., reduced greasy/sticky feel) on dry hair; and free flowing (i.e., reduced clumpy hair) on dry hair.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. The weight average molecular weight may be measured by gel permeation chromatography.

"QS" means sufficient quantity for 100%.

Hair Conditioning Compositions

The hair conditioning composition of the present invention comprises: a cationic surfactant; a high melting point fatty compound; an aqueous carrier; a cyclic compound selected from the group consisting of Vitamin B3 compound, Xanthine compound, Salicylic acid ester, and mixtures thereof; and a compound having at least three large head groups. It is believed that the combination of the specific cyclic compounds and the compound having at least three large head groups provides improved hair manageability, for example, improved hair alignment on dry hair after combing, reduced volume on dry hair (especially at the bottom side of hair) after combing, and/or curl-in hair tips after combing on dry hair. It also is believed that the combination of the specific cyclic compounds and the compound having at least three large head groups may also provide at least one of the followings: improved spreadability; reduced sliminess on wet hair; and improved clean feel (i.e., reduced greasy/sticky feel) on dry hair; and free flowing (i.e., reduced clumpy hair) on dry hair, while providing the above hair manageability.

Cyclic Compounds

The composition of the present invention comprises cyclic compounds selected from the group consisting of Vitamin B3 compounds, Xanthine compounds, Salicylic acid esters, and mixtures thereof. The cyclic compounds can be included in the hair conditioning composition at a level of from about 0.2%, preferably from about 0.5%, more preferably from about 0.6% in view of providing hair manageability, and to about 10%, preferably to about 5%, more preferably to about 4%, still more preferably to about 3% in view of hair manageability especially hair alignment after combing.

(1) Vitamin B3 Compound

As used herein, "vitamin B3 compound" means one or more compounds having the formula:

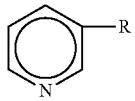

wherein R is —$CONH_2$ (i.e., niacinamide), —COOH (i.e., nicotinic acid) or —$CH_2OH$ (i.e., nicotinyl alcohol); derivatives thereof; mixtures thereof; and salts of any of the foregoing.

Exemplary derivatives of the foregoing vitamin B3 compounds include nicotinic acid esters, including non-vasodilating esters of nicotinic acid (e.g, tocopherol nicotinate, and myristyl nicotinate), nicotinyl amino acids, nicotinyl alcohol esters of carboxylic acids, nicotinic acid N-oxide and niacinamide N-oxide.

Preferred vitamin B3 compounds are niacinamide, in view of providing the benefits of the present invention, and also in view of the stability in the composition as other vitamin B3 products such as nicotinic acid esters may be decomposed to nicotinic acids.

(2) Xanthine Compound

As used herein, "xanthine compound" means one or more xanthines, derivatives thereof, and mixtures thereof. Xanthine Compounds that can be useful herein include, but are not limited to, caffeine, xanthine, 1-methyl xanthine, theophylline, theobromine, derivatives thereof, and mixtures thereof. Among these compounds, caffeine is preferred in view of providing the benefit of the present invention, maybe in view of its solubility in the composition.

(3) Salicylic Acid Ester

As used herein, "Salicylic acid ester" means one or more compounds having the following structure:

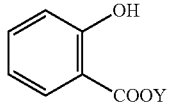

wherein Y is linear or branched alkyl having from about 1 to about 25 carbon atoms, preferably from about 2 to about 15 carbon atoms, more preferably from about 3 to about 10 carbon atoms. Highly preferred herein are those having a branched alkyl as Y. Among them, further preferred is ethylhexylsalicylate.

Compound Having at Least Three Large Head Groups

The composition of the present invention comprises a compound having at least three large head groups. The compound can be included in the hair conditioning composition at a level of from about 0.1%, preferably from about 0.2%, more preferably from about 0.5%, in view of providing hair manageability, and to about 15%, preferably to about 10%, more preferably to about 8%, still more preferably to about 5% in view of providing improved clean feel (i.e., reduced greasy/sticky feel) on dry hair, and/or free flowing (i.e., reduced clumpy hair) on dry hair.

Also, in view of providing the benefit of the present invention, it is preferred that the weight ratio of the above cyclic compounds to this compound having at least three large head groups is from about 0.3:1 to about 2.2:1, more preferably, from about 0.4:1 to about 2:1, still more preferably from about 0.4:1 to about 1.8:1, even more preferably from about 0.5:1 to about 1.4:1. When the ratio of the cyclic compounds is too high, the composition may cause phase separation. When the ratio of the compound having at least three large head groups is too high, the composition tends to have reduced spreadability on hair.

Preferred are those in liquid at 25° C., more preferably at 15° C., still more preferably at 11° C.

The compounds useful herein are those having at least three large head groups, preferably at least three hydrocarbon groups wherein each of the hydrocarbon groups has from about 5 to about 50 carbons, more preferably from about 6 to about 40 carbons, still more preferably from about 6 to about 35 carbons.

The total number of the carbon atoms of such at least three large head groups preferably hydrocarbon groups are, preferably from about 15 to about 150, more preferably from about 18 to about 120, still more preferably from about 18 to about 105.

The 3 hydrocarbon groups are independently, branched, straight, saturated, or unsaturated alkyl, aryl, and alkylaryl groups.

It has been surprisingly found by the inventors of the present invention that, differently from di-esters having two large head groups being hydrocarbons or mono-esters having one large head group being hydrocarbons, the compounds of the present invention having at least three large head groups such as hydrocarbons have synergy effect with the specific cyclic compounds above described and provides the benefits of the present invention.

Such compounds useful herein are, for example, triesters. Such triesters include, for example, glycerol triesters having the following formula:

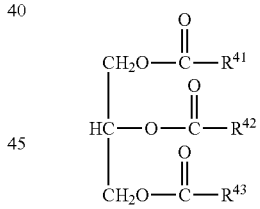

wherein $R^{41}$, $R^{42}$, and $R^{43}$, are explained above as three large head groups. Such glycerol triesters include, for example, trioctanoin (also known as glycerol trioctanoate or caprylic acid triglyceride). Such triesters also include, for example, trimethylol triesters having the following formula:

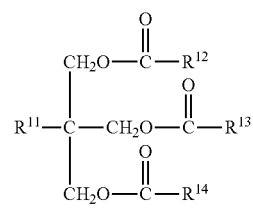

wherein $R^{11}$ is H, $CH_3$ or $C_2H_5$, and $R^{12}$, $R^{13}$, and $R^{14}$ are explained above as three large head groups.

Such triesters further include, for example, citrate triester the following formula:

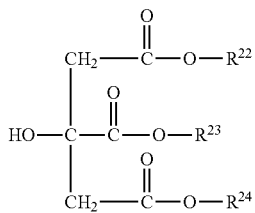

wherein $R^{22}$, $R^{23}$, and $R^{24}$, are explained above as three large head groups.

Another example of the compounds herein can be alkyl glutamate diesters having the following formula:

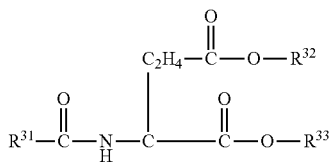

wherein $R^{31}$, $R^{32}$, and $R^{33}$, are explained above as three large head groups. Such alkyl glutamate diesters are, for example, Phytosteryl/Octyldodecyl Lauroyl Glutamate in which lauroyl corresponds to $R^{31}$, Phytosteryl corresponds to $R^{32}$ Octyl dodecyl corresponds to $R^{33}$. Such Phytosteryl/Octyldodecyl Lauroyl Glutamate can be supplied from, for example, Ajinomoto with a tradename Eldew PS-203.

Among the above exemplified compounds, preferred are glycerol triesters and alkyl glutamate diesters, more preferred are glycerol triesters.

Cationic Surfactant

The compositions of the present invention comprise a cationic surfactant. The cationic surfactant can be included in the composition at a level of from about 1.0%, preferably from about 1.5%, more preferably from about 2.0%, still more preferably from about 3.0%, and to about 25%, preferably to about 10%, more preferably to about 8.0%, still more preferably to about 6.0% by weight of the composition, in view of providing the benefits of the present invention.

Preferably, in the present invention, the surfactant is water-insoluble. In the present invention, "water-insoluble surfactants" means that the surfactants have a solubility in water at 25° C. of preferably below 0.5 g/100 g (excluding 0.5 g/100 g) water, more preferably 0.3 g/100 g water or less.

Cationic surfactant useful herein can be one cationic surfactant or a mixture of two or more cationic surfactants. Preferably, the cationic surfactant is selected from: a mono-long alkyl quaternized ammonium salt; a combination of a mono-long alkyl quaternized ammonium salt and a di-long alkyl quaternized ammonium salt; a mono-long alkyl amine; a combination of a mono-long alkyl amine and a di-long alkyl quaternized ammonium salt; and a combination of a mono-long alkyl amine and a mono-long alkyl quaternized ammonium salt.

Mono-Long Alkyl Amine

Mono-long alkyl amine useful herein are those having one long alkyl chain of preferably from 12 to 30 carbon atoms, more preferably from 16 to 24 carbon atoms, still more preferably from 18 to 22 alkyl group. Mono-long alkyl amines useful herein also include mono-long alkyl amidoamines. Primary, secondary, and tertiary fatty amines are useful.

Particularly useful are tertiary amido amines having an alkyl group of from about 12 to about 22 carbons. Exemplary tertiary amido amines include: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, diethylaminoethylstearamide. Useful amines in the present invention are disclosed in U.S. Pat. No. 4,275,055, Nachtigal, et al.

These amines are used in combination with acids such as l-glutamic acid, lactic acid, hydrochloric acid, malic acid, succinic acid, acetic acid, fumaric acid, tartaric acid, citric acid, l-glutamic hydrochloride, maleic acid, and mixtures thereof; more preferably l-glutamic acid, lactic acid, citric acid, at a molar ratio of the amine to the acid of from about 1:0.3 to about 1:2, more preferably from about 1:0.4 to about 1:1.

Mono-Long Alkyl Quaternized Ammonium Salt

The mono-long alkyl quaternized ammonium salts useful herein are those having one long alkyl chain which has from 12 to 30 carbon atoms, preferably from 16 to 24 carbon atoms, more preferably $C_{18-22}$ alkyl group. The remaining groups attached to nitrogen are independently selected from an alkyl group of from 1 to about 4 carbon atoms or an alkoxy, polyoxyalkylene, alkylamido, hydroxyalkyl, aryl or alkylaryl group having up to about 4 carbon atoms.

Mono-long alkyl quaternized ammonium salts useful herein are those having the formula (I):

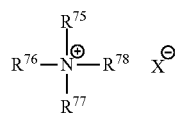

wherein one of $R^{75}$, $R^{76}$, $R^{77}$ and $R^{78}$ is selected from an alkyl group of from 12 to 30 carbon atoms or an aromatic, alkoxy, polyoxyalkylene, alkylamido, hydroxyalkyl, aryl or alkylaryl group having up to about 30 carbon atoms; the remainder of $R^{75}$, $R^{76}$, $R^{77}$ and $R^{78}$ are independently selected from an alkyl group of from 1 to about 4 carbon atoms or an alkoxy, polyoxyalkylene, alkylamido, hydroxyalkyl, aryl or alkylaryl group having up to about 4 carbon atoms; and $X^-$ is a salt-forming anion such as those selected from halogen, (e.g. chloride, bromide), acetate, citrate, lactate, glycolate, phosphate, nitrate, sulfonate, sulfate, alkylsulfate, and alkyl sulfonate radicals. The alkyl groups can contain, in addition to carbon and hydrogen atoms, ether and/or ester linkages, and other groups such as amino groups. The longer chain alkyl groups, e.g., those of about 12 carbons, or higher, can be saturated or unsaturated. Preferably, one of $R^{75}$, $R^{76}$, $R^{77}$ and $R^{78}$ is selected from an alkyl group of from 12 to 30 carbon atoms, more preferably from 16 to 24 carbon atoms, still more preferably from 18 to 22 carbon atoms, even more preferably 22 carbon atoms; the remainder of $R^{75}$, $R^{76}$, $R^{77}$ and $R^{78}$ are independently selected from CH₃, C₂H₅, C₂H₄OH, and mixtures thereof; and X is selected from the group consisting of Cl, Br, CH₃OSO₃, C₂H₅OSO₃, and mixtures thereof.

Nonlimiting examples of such mono-long alkyl quaternized ammonium salt cationic surfactants include: behenyl trimethyl ammonium salt; stearyl trimethyl ammonium salt; cetyl trimethyl ammonium salt; and hydrogenated tallow alkyl trimethyl ammonium salt.

Di-Long Alkyl Quaternized Ammonium Salts

When used, di-long alkyl quaternized ammonium salts are preferably combined with a mono-long alkyl quaternized ammonium salt and/or mono-long alkyl amine salt, at the weight ratio of from 1:1 to 1:5, more preferably from 1:1.2 to 1:5, still more preferably from 1:1.5 to 1:4, in view of stability in rheology and conditioning benefits.

Di-long alkyl quaternized ammonium salts useful herein are those having two long alkyl chains of from 12 to 30 carbon atoms, more preferably from 16 to 24 carbon atoms, still more preferably from 18 to 22 carbon atoms. Such di-long alkyl quaternized ammonium salts useful herein are those having the formula (I):

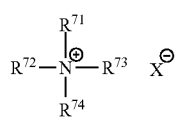

(I)

wherein two of $R^{71}$, $R^{72}$, $R^{73}$ and $R^{74}$ are selected from an aliphatic group of from 12 to 30 carbon atoms, preferably from 16 to 24 carbon atoms, more preferably from 18 to 22 carbon atoms or an aromatic, alkoxy, polyoxyalkylene, alkylamido, hydroxyalkyl, aryl or alkylaryl group having up to about 30 carbon atoms; the remainder of $R^{71}$, $R^{72}$, $R^{73}$ and $R^{74}$ are independently selected from an aliphatic group of from 1 to about 8 carbon atoms, preferably from 1 to 3 carbon atoms or an aromatic, alkoxy, polyoxyalkylene, alkylamido, hydroxyalkyl, aryl or alkylaryl group having up to about 8 carbon atoms; and X⁻ is a salt-forming anion selected from the group consisting of halides such as chloride and bromide, $C_1$-$C_4$ alkyl sulfate such as methosulfate and ethosulfate, and mixtures thereof. The aliphatic groups can contain, in addition to carbon and hydrogen atoms, ether linkages, and other groups such as amino groups. The longer chain aliphatic groups, e.g., those of about 16 carbons, or higher, can be saturated or unsaturated. Preferably, two of $R^{71}$, $R^{72}$, $R^{73}$ and $R^{74}$ are selected from an alkyl group of from 12 to 30 carbon atoms, preferably from 16 to 24 carbon atoms, more preferably from 18 to 22 carbon atoms; and the remainder of $R^{71}$, $R^{72}$, $R^{73}$ and $R^{74}$ are independently selected from CH₃, C₂H₅, C₂H₄OH, CH₂C₆H₅, and mixtures thereof.

Such preferred di-long alkyl cationic surfactants include, for example, dialkyl (14-18) dimethyl ammonium chloride, ditallow alkyl dimethyl ammonium chloride, dihydrogenated tallow alkyl dimethyl ammonium chloride, distearyl dimethyl ammonium chloride, and dicetyl dimethyl ammonium chloride.

High Melting Point Fatty Compound

The composition of the present invention comprises a high melting point fatty compound. The high melting point fatty compound can be included in the composition at a level of from about 2.5%, preferably from about 3.0%, more preferably from about 4.0%, still more preferably from about 5.0%, and to about 30%, preferably to about 10%, more preferably to about 8.0% by weight of the composition, in view of providing the benefits of the present invention.

The high melting point fatty compound useful herein have a melting point of 25° C. or higher, preferably 40° C. or higher, more preferably 45° C. or higher, still more preferably 50° C. or higher, in view of stability of the emulsion especially the gel matrix. Preferably, such melting point is up to about 90° C., more preferably up to about 80° C., still more preferably up to about 70° C., even more preferably up to about 65° C., in view of easier manufacturing and easier emulsification. In the present invention, the high melting point fatty compound can be used as a single compound or as a blend or mixture of at least two high melting point fatty compounds. When used as such blend or mixture, the above melting point means the melting point of the blend or mixture.

The high melting point fatty compound useful herein is selected from the group consisting of fatty alcohols, fatty acids, fatty alcohol derivatives, fatty acid derivatives, and mixtures thereof. It is understood by the artisan that the compounds disclosed in this section of the specification can in some instances fall into more than one classification, e.g., some fatty alcohol derivatives can also be classified as fatty acid derivatives. However, a given classification is not intended to be a limitation on that particular compound, but is done so for convenience of classification and nomenclature. Further, it is understood by the artisan that, depending on the number and position of double bonds, and length and position of the branches, certain compounds having certain required carbon atoms may have a melting point of less than the above preferred in the present invention. Such compounds of low melting point are not intended to be included in this section. Nonlimiting examples of the high melting point compounds are found in International Cosmetic Ingredient Dictionary, Fifth Edition, 1993, and CTFA Cosmetic Ingredient Handbook, Second Edition, 1992.

Among a variety of high melting point fatty compounds, fatty alcohols are preferably used in the composition of the present invention. The fatty alcohols useful herein are those having from about 14 to about 30 carbon atoms, preferably from about 16 to about 22 carbon atoms. These fatty alcohols are saturated and can be straight or branched chain alcohols.

Preferred fatty alcohols include, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group.

In the present invention, more preferred fatty alcohol is a mixture of cetyl alcohol and stearyl alcohol.

Generally, in the mixture, the weight ratio of cetyl alcohol to stearyl alcohol is preferably from about 1:9 to 9:1, more preferably from about 1:4 to about 4:1, still more preferably from about 1:2.3 to about 1.5:1.

When using higher level of total cationic surfactant and high melting point fatty compounds, the mixture has the weight ratio of cetyl alcohol to stearyl alcohol of preferably from about 1:1 to about 4:1, more preferably from about 1:1 to about 2:1, still more preferably from about 1.2:1 to about 2:1, in view of avoiding to get too thick for spreadability. It may also provide more conditioning on damaged part of the hair.

Aqueous Carrier

The composition of the present invention comprises an aqueous carrier. The level and species of the carrier are selected according to the compatibility with other components, and other desired characteristic of the product.

The carrier useful in the present invention includes water and water solutions of lower alkyl alcohols. The lower alkyl alcohols useful herein are monohydric alcohols having 1 to 6 carbons, more preferably ethanol and isopropanol.

Preferably, the aqueous carrier is substantially water. Deionized water is preferably used. Water from natural sources including mineral cations can also be used, depending on the desired characteristic of the product. Generally, the compositions of the present invention comprise from about 40% to about 99%, preferably from about 50% to about 95%, and more preferably from about 70% to about 90%, and more preferably from about 80% to about 90% aqueous carrier, preferably water.

Gel Matrix

Preferably, in the present invention, a gel matrix is formed by the cationic surfactant, the high melting point fatty compound, and an aqueous carrier. The gel matrix is suitable for providing various conditioning benefits, such as slippery feel during the application to wet hair and softness and moisturized feel on dry hair. Also, when combining this gel matrix with the above cyclic compound and the compound having at least three large head groups, the composition provides improved spreadability which is believed to provide more balanced deposition of hair conditioning agents both on hair tips and hair root and thus deliver further improved hair manageability.

Preferably, when the gel matrix is formed, the cationic surfactant and the high melting point fatty compound are contained at a level such that the weight ratio of the cationic surfactant to the high melting point fatty compound is in the range of, preferably from about 1:1 to about 1:10, more preferably from about 1:1.5 to about 1:7, still more preferably from about 1:2 to about 1:6, in view of providing improved wet conditioning benefits.

Preferably, when the gel matrix is formed, the composition of the present invention is substantially free of anionic surfactants, in view of stability of the gel matrix. In the present invention, "the composition being substantially free of anionic surfactants" means that: the composition is free of anionic surfactants; or, if the composition contains anionic surfactants, the level of such anionic surfactants is very low. In the present invention, a total level of such anionic surfactants, if included, preferably 1% or less, more preferably 0.5% or less, still more preferably 0.1% or less by weight of the composition. Most preferably, the total level of such anionic surfactants is 0% by weight of the composition.

Silicone Compound

The compositions of the present invention may further contain a silicone compound. It is believed that the silicone compound can provide smoothness and softness on dry hair. The silicone compounds herein can be used at levels by weight of the composition of preferably from about 0.1% to about 20%, more preferably from about 0.5% to about 10%, still more preferably from about 1% to about 8%.

Preferably, the silicone compounds have an average particle size of from about 1 microns to about 50 microns, in the composition.

The silicone compounds useful herein, as a single compound, as a blend or mixture of at least two silicone compounds, or as a blend or mixture of at least one silicone compound and at least one solvent, have a viscosity of preferably from about 1,000 to about 2,000,000 mPa·s at 25° C.

The viscosity can be measured by means of a glass capillary viscometer as set forth in Dow Corning Corporate Test Method CTM0004, Jul. 20, 1970. Suitable silicone fluids include polyalkyl siloxanes, polyaryl siloxanes, polyalkylaryl siloxanes, polyether siloxane copolymers, amino substituted silicones, quaternized silicones, and mixtures thereof. Other nonvolatile silicone compounds having conditioning properties can also be used.

Preferred polyalkyl siloxanes include, for example, polydimethylsiloxane, polydiethylsiloxane, and polymethylphenylsiloxane. Polydimethylsiloxane, which is also known as dimethicone, is especially preferred.

The above polyalkylsiloxanes are available, for example, as a mixture with silicone compounds having a lower viscosity. Such mixtures have a viscosity of preferably from about 1,000 mPa·s to about 100,000 mPa·s, more preferably from about 5,000 mPa·s to about 50,000 mPa·s. Such mixtures preferably comprise: (i) a first silicone having a viscosity of from about 100,000 mPa·s to about 30,000,000 mPa·s at 25° C., preferably from about 100,000 mPa·s to about 20,000,000 mPa·s; and (ii) a second silicone having a viscosity of from about 5 mPa·s to about 10,000 mPa·s at 25° C., preferably from about 5 mPa·s to about 5,000 mPa·s. Such mixtures useful herein include, for example, a blend of dimethicone having a viscosity of 18,000,000 mPa·s and dimethicone having a viscosity of 200 mPa·s available from GE Toshiba, and a blend of dimethicone having a viscosity of 18,000,000 mPa·s and cyclopentasiloxane available from GE Toshiba.

The silicone compounds useful herein also include a silicone gum. The term "silicone gum", as used herein, means a polyorganosiloxane material having a viscosity at 25° C. of greater than or equal to 1,000,000 centistokes. It is recognized that the silicone gums described herein can also have some overlap with the above-disclosed silicone compounds. This overlap is not intended as a limitation on any of these materials. The "silicone gums" will typically have a mass molecular weight in excess of about 200,000, generally between about 200,000 and about 1,000,000. Specific examples include polydimethylsiloxane, poly(dimethylsiloxane methylvinylsiloxane) copolymer, poly(dimethylsiloxane diphenylsiloxane methylvinylsiloxane) copolymer and mixtures thereof. The silicone gums are available, for example, as a mixture with silicone compounds having a lower viscosity. Such mixtures useful herein include, for example, Gum/Cyclomethicone blend available from Shin-Etsu.

Silicone compounds useful herein also include amino substituted materials. Preferred aminosilicones include, for example, those which conform to the general formula (I):

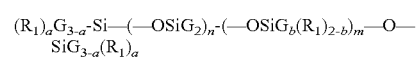

wherein G is hydrogen, phenyl, hydroxy, or $C_1$-$C_8$ alkyl, preferably methyl; a is 0 or an integer having a value from 1 to 3, preferably 1; b is 0, 1 or 2, preferably 1; n is a number from 0 to 1,999; m is an integer from 0 to 1,999; the sum of n and m is a number from 1 to 2,000; a and m are not both 0; $R_1$ is a monovalent radical conforming to the general formula $C_qH_{2q}L$, wherein q is an integer having a value from 2 to 8 and L is selected from the following groups: —N($R_2$)$CH_2$—$CH_2$—N($R_2$)$_2$; —N($R_2$)$_2$; —N($R_2$)$_3A^-$; —N($R_2$)$CH_2$—$CH_2$—$NR_2H_2A^-$; wherein $R_2$ is hydrogen, phenyl, benzyl, or a saturated hydrocarbon radical, preferably an alkyl radical from about $C_1$ to about $C_{20}$; $A^-$ is a halide ion.

Highly preferred amino silicones are those corresponding to formula (I) wherein m=0, a=1, q=3, G=methyl, n is preferably from about 1500 to about 1700, more preferably about 1600; and L is —N(CH$_3$)$_2$ or —NH$_2$, more preferably —NH$_2$. Another highly preferred amino silicones are those corresponding to formula (I) wherein m=0, a=1, q=3, G=methyl, n is preferably from about 400 to about 600, more preferably about 500; and L is —N(CH$_3$)$_2$ or —NH$_2$, more preferably —NH$_2$. Such highly preferred amino silicones can be called as terminal aminosilicones, as one or both ends of the silicone chain are terminated by nitrogen containing group.

The above aminosilicones, when incorporated into the composition, can be mixed with solvent having a lower viscosity. Such solvents include, for example, polar or non-polar, volatile or non-volatile oils. Such oils include, for example, silicone oils, hydrocarbons, and esters. Among such a variety of solvents, preferred are those selected from the group consisting of non-polar, volatile hydrocarbons, volatile cyclic silicones, non-volatile linear silicones, and mixtures thereof. The non-volatile linear silicones useful herein are those having a viscosity of from about 1 to about 20,000 centistokes, preferably from about 20 to about 10,000 centistokes at 25° C. Among the preferred solvents, highly preferred are non-polar, volatile hydrocarbons, especially non-polar, volatile isoparaffins, in view of reducing the viscosity of the aminosilicones and providing improved hair conditioning benefits such as reduced friction on dry hair. Such mixtures have a viscosity of preferably from about 1,000 mPa·s to about 100,000 mPa·s, more preferably from about 5,000 mPa·s to about 50,000 mPa·s.

Other suitable alkylamino substituted silicone compounds include those having alkylamino substitutions as pendant groups of a silicone backbone. Highly preferred are those known as "amodimethicone". Commercially available amodimethicones useful herein include, for example, BY16-872 available from Dow Corning.

The silicone compounds may further be incorporated in the present composition in the form of an emulsion, wherein the emulsion is made my mechanical mixing, or in the stage of synthesis through emulsion polymerization, with or without the aid of a surfactant selected from anionic surfactants, nonionic surfactants, cationic surfactants, and mixtures thereof.

Silicone Polymer Containing Quaternary Groups

Silicone compounds useful herein include, for example, a Silicone Polymer Containing Quaternary Groups comprising terminal ester groups, having a viscosity up to 100,000 mPa·s and a D block length of greater than 200 D units. Without being bound by theory, this low viscosity silicone polymer provides improved conditioning benefits such as smooth feel, reduced friction, and prevention of hair damage, while eliminating the need for a silicone blend.

Structurally, the silicone polymer is a polyorganosiloxane compound comprising one or more quaternary ammonium groups, at least one silicone block comprising greater than 200 siloxane units, at least one polyalkylene oxide structural unit, and at least one terminal ester group. In one or more embodiments, the silicone block may comprise between 300 to 500 siloxane units.

The silicone polymer is present in an amount of from about 0.05% to about 15%, preferably from about 0.1% to about 10%, more preferably from about 0.15% to about 5%, and even more preferably from about 0.2% to about 4% by weight of the composition.

In a preferred embodiment, the polyorganosiloxane compounds have the general formulas (Ia) and (Ib):

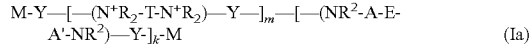

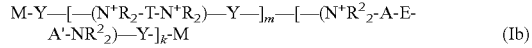

wherein:

m is >0, preferred 0.01 to 100, more preferred 0.1 to 100, even more preferred 1 to 100, specifically 1 to 50, more specifically 1 to 20, even more specifically 1 to 10, k is 0 or an average value of from >0 to 50, or preferably from 1 to 20, or even more preferably from 1 to 10, M represents a terminal group, comprising terminal ester groups selected from

—OC(O)—Z

—OS(O)$_2$—Z

—OS(O$_2$)O—Z

—OP(O)(O—Z)OH

—OP(O)(O—Z) 2 wherein Z is selected from monovalent organic residues having up to 40 carbon atoms, optionally comprising one or more hetero atoms.

A and A' each are independently from each other selected from a single bond or a divalent organic group having up to 10 carbon atoms and one or more hetero atoms, and E is a polyalkylene oxide group of the general formula:

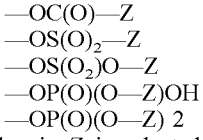

wherein q=0 to 200, r=0 to 200, s=0 to 200, and q+r+s=1 to 600.

$R^2$ is selected from hydrogen or R,

R is selected from monovalent organic groups having up to 22 carbon atoms and optionally one or more heteroatoms, and wherein the free valencies at the nitrogen atoms are bound to carbon atoms, Y is a group of the formula:

with

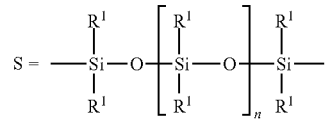

wherein R1=$C_1$-$C_{22}$-alkyl, $C_1$-$C_{22}$-fluoralkyl or aryl; n=200 to 1000, and these can be identical or different if several S Groups are present in the polyorganosiloxane compound.

K is a bivalent or trivalent straight chain, cyclic and/or branched $C_2$-$C_{40}$ hydrocarbon residue which is optionally interrupted by —O—, —NH—, trivalent N, —NR$^1$—, —C(O)—, —C(S)—, and optionally substituted with —OH, wherein R$^1$ is defined as above, T is selected from a divalent organic group having up to 20 carbon atoms and one or more hetero atoms.

The residues K may be identical or different from each other. In the —K—S—K— moiety, the residue K is bound to the silicon atom of the residue S via a C—Si-bond.

Due to the possible presence of amine groups (—(NR$^2$-A-E-A'-NR$^2$)—) in the polyorganosiloxane compounds, they may have protonated ammonium groups, resulting from the protonation of such amine groups with organic or inorganic acids. Such compounds are sometimes referred to as acid addition salts of the polyorganosiloxane compounds.

In a preferred embodiment the molar ratio of the quaternary ammonium groups b) and the terminal ester groups c) is less than 100:20, even more preferred is less than 100:30 and is most preferred less than 100:50. The ratio can be determined by $^{13}$C-NMR.

In a further embodiment, the polyorganosiloxane composition may comprise:

A) at least one polyorganosiloxane compound, comprising a) at least one polyorganosiloxane group, b) at least one quaternary ammonium group, c) at least one terminal ester group, and d) at least one polyalkylene oxide group (as defined before), B) at least one polyorganosiloxane compound, comprising at least one terminal ester group, different from compound A).

In the definition of component A) it can be referred to the description of the polyorganosiloxane compounds of the invention. The polyorganosiloxane compound B) differs from the polyorganosiloxane compound A) preferably in that it does not comprise quaternary ammonium groups. Preferred polyorganosiloxane compounds B) result from the reaction of monofunctional organic acids, in particular carboxylic acids, and polyorganosiloxane containing bisepoxides.

In the polyorganosiloxane compositions the weight ratio of compound A) to compound B) is preferably less than 90:10. Or in other words, the content of component B) is at least 10 weight percent. In a further preferred embodiment of the polyorganosiloxane compositions in compound A) the molar ratio of the quaternary ammonium groups b) and the terminal ester groups c) is less than 100:10, even more preferred is less than 100:15 and is most preferred less than 100:20.

The silicone polymer has a viscosity at 20° C. and a shear rate of 0.1 s$^{-1}$ (plate-plate system, plate diameter 40 mm, gap width 0.5 mm) of less than 100,000 mPa·s (100 Pa·s). In further embodiments, the viscosities of the neat silicone polymers may range from 500 to 100,000 mPa·s, or preferably from 500 to 70,000 mPa·s, or more preferably from 500 to 50,000 mPa·s, or even more preferably from 500 to 20,000 mPa·s. In further embodiments, the viscosities of the neat polymers may range from 500 to 10,000 mPa·s, or preferably 500 to 5000 mPa·s determined at 20° C. and a shear rate of 0.1 s$^{-1}$.

In addition to the above listed silicone polymers, the following preferred compositions are provided below. For example, in the polyalkylene oxide group E of the general formula:

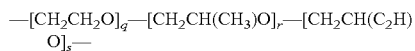

—[CH$_2$CH$_2$O]$_q$—[CH$_2$CH(CH$_3$)O]$_r$—[CH$_2$CH(C$_2$H)O]$_s$— wherein the q, r, and s indices may be defined as follows: q=0 to 200, or preferably from 0 to 100, or more preferably from 0 to 50, or even more preferably from 0 to 20, r=0 to 200, or preferably from 0 to 100, or more preferably from 0 to 50, or even more preferably from 0 to 20, s=0 to 200, or preferably from 0 to 100, or more preferably from 0 to 50, or even more preferably from 0 to 20, and q+r+s=1 to 600, or preferably from 1 to 100, or more preferably from 1 to 50, or even more preferably from 1 to 40.

For polyorganosiloxane structural units with the general formula S:

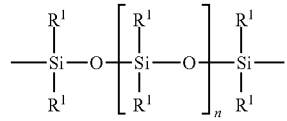

$R^1$=C$_1$-C$_{22}$-alkyl, C$_1$-C$_{22}$-fluoralkyl or aryl; n=from 200 to 1000, or preferably from 300 to 500, K (in the group —K—S—K—) is preferably a bivalent or trivalent straight chain, cyclical or branched C$_2$-C$_{20}$ hydrocarbon residue which is optionally interrupted by —O—, —NH—, trivalent N, —NR$^1$—, —C(O)—, —C(S)—, and optionally substituted with —OH.

In specific embodiments, $R^1$ is C$_1$-C$_{18}$ alkyl, C$_1$-C$_{18}$ fluoroalkyl and aryl. Furthermore, $R^1$ is preferably C$_1$-C$_{18}$ alkyl, C$_1$-C$_6$ fluoroalkyl and aryl. Furthermore, $R^1$ is more preferably C$_1$-C$_6$ alkyl, C$_1$-C$_6$ fluoroalkyl, even more preferably C$_1$-C$_4$ fluoroalkyl, and phenyl. Most preferably, $R^1$ is methyl, ethyl, trifluoropropyl and phenyl.

As used herein, the term "C$_1$-C$_{22}$ alkyl" means that the aliphatic hydrocarbon groups possess from 1 to 22 carbon atoms which can be straight chain or branched. Methyl, ethyl, propyl, n-butyl, pentyl, hexyl, heptyl, nonyl, decyl, undecyl, isopropyl, neopentyl and 1,2,3-trimethyl hexyl moieties serve as examples.

Further as used herein, the term "C$_1$-C$_{22}$ fluoroalkyl" means aliphatic hydrocarbon compounds with 1 to 22 carbon atoms which can be straight chain or branched and are substituted with at least one fluorine atom. Monofluormethyl, monofluoroethyl, 1,1,1-trifluorethyl, perfluoroethyl, 1,1,1-trifluoropropyl, 1,2,2-trifluorobutyl are suitable examples.

Moreover, the term "aryl" means unsubstituted or phenyl substituted once or several times with OH, F, Cl, CF$_3$, C$_1$-C$_6$ alkyl, C$_1$-C$_6$ alkoxy, C$_3$-C$_7$ cycloalkyl, C$_2$-C$_6$ alkenyl or phenyl. Aryl may also mean naphthyl.

For the embodiments of the polyorganosiloxanes, the positive charges resulting from the ammonium group(s), are neutralized with inorganic anions such as chloride, bromide, hydrogen sulfate, sulfate, or organic anions, like carboxylates deriving from C$_1$-C$_{30}$ carboxylic acids, for example acetate, propionate, octanoate, especially from C$_{10}$-C$_{18}$ carboxylic acids, for example decanoate, dodecanoate, tetradecanoate, hexadecanoate, octadecanoate and oleate, alkylpolyethercarboxylate, alkylsulphonate, arylsulphonate, alkylarylsulphonate, alkylsulphate, alkylpolyethersulphate, phosphates derived from phosphoric acid mono alkyl/aryl ester and phosphoric acid dialkyl/aryl ester. The properties of the polyorganosiloxane compounds can be, inter alia, modified based upon the selection of acids used.

The quaternary ammonium groups are usually generated by reacting the di-tertiary amines with an alkylating agents, selected from in particular di-epoxides (sometimes referred to also as bis-epoxides) in the presence of mono carboxylic acids and difunctional dihalogen alkyl compounds.

In a preferred embodiment the polyorganosiloxane compounds are of the general formulas (Ia) and (Ib):

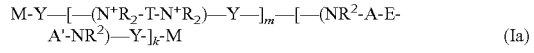

M-Y—[—(N$^+$R$_2$-T-N$^+$R$_2$)—Y—]$_m$—[—(NR$^2$-A-E-A'-NR$^2$)—Y-]$_k$-M     (Ia)

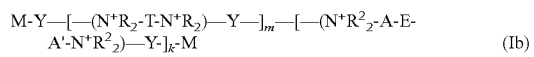

M-Y—[—(N$^+$R$_2$-T-N$^+$R$_2$)—Y—]$_m$—[—(N$^+$R$^2$$_2$-A-E-A'-N$^+$R$^2$$_2$)—Y-]$_k$-M     (Ib)

wherein each group is as defined above; however, the repeating units are in a statistical arrangement (i.e., not a block-wise arrangement).

In a further preferred embodiment the polyorganosiloxane compounds may be also of the general formulas (IIa) or (IIb):

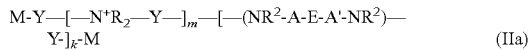

$$M\text{-}Y\text{—}[\text{—}N^+R_2\text{—}Y\text{—}]_m\text{—}[\text{—}(NR^2\text{-}A\text{-}E\text{-}A'\text{-}NR^2)\text{—}Y\text{-}]_k\text{-}M \quad \text{(IIa)}$$

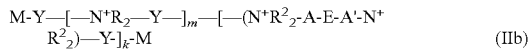

$$M\text{-}Y\text{—}[\text{—}N^+R_2\text{—}Y\text{—}]_m\text{—}[\text{—}(N^+R^2{}_2\text{-}A\text{-}E\text{-}A'\text{-}N^+R^2{}_2)\text{—}Y\text{-}]_k\text{-}M \quad \text{(IIb)}$$

wherein each group is as defined above. Also in such formula the repeating units are usually in a statistical arrangement (i.e. not a block-wise arrangement).

wherein, as defined above, M is

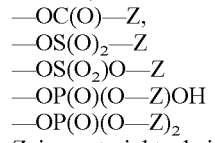

—OC(O)—Z,
—OS(O)$_2$—Z
—OS(O$_2$)O—Z
—OP(O)(O—Z)OH
—OP(O)(O—Z)$_2$

Z is a straight chain, cyclic or branched saturated or unsaturated $C_1$-$C_{20}$, or preferably $C_2$ to $C_{18}$, or even more preferably a hydrocarbon radical, which can be interrupted by one or more —O—, or —C(O)— and substituted with —OH. In a specific embodiment, M is —OC(O)—Z resulting from normal carboxylic acids in particular with more than 10 carbon atoms like for example dodecanoic acid.

In a further embodiment, the molar ratio of the polyorganosiloxane-containing repeating group —K—S—K— and the polyalkylene repeating group -A-E-A'- or -A'-E-A- is between 100:1 and 1:100, or preferably between 20:1 and 1:20, or more preferably between 10:1 and 1:10.

In the group —(N$^+$R$_2$-T-N$^+$R$_2$)—, R may represent a monovalent straight chain, cyclic or branched $C_1$-$C_{20}$ hydrocarbon radical, which can be interrupted by one or more —O—, —C(O)— and can be substituted by —OH, T may represent a divalent straight-chain, cyclic, or branched $C_1$-$C_{20}$ hydrocarbon radical, which can be interrupted by —O—, —C(O)— and can be substituted by hydroxyl.

The above described polyorganosiloxane compounds comprising quaternary ammonium functions and ester functions may also contain: 1) individual molecules which contain quaternary ammonium functions and no ester functions; 2) molecules which contain quaternary ammonium functions and ester functions; and 3) molecules which contain ester functions and no quaternary ammonium functions. While not limited to structure, the above described polyorganosiloxane compounds comprising quaternary ammonium functions and ester functions are to be understood as mixtures of molecules comprising a certain averaged amount and ratio of both moieties.

Various monofunctional organic acids may be utilized to yield the esters. Exemplary embodiments include $C_1$-$C_{30}$ carboxylic acids, for example $C_2$, $C_3$, $C_8$ acids, $C_{10}$-$C_{18}$ carboxylic acids, for example $C_{12}$, $C_{14}$, $C_{16}$ acids, saturated, unsaturated and hydroxyl functionalized $C_{18}$ acids, alkylpolyethercarboxylic acids, alkylsulphonic acids, arylsulphonic acids, alkylarylsulphonic acids, alkylsulphuric acids, alkylpolyethersulphuric acids, phosphoric acid mono alkyl/aryl esters and phosphoric acid dialkyl/aryl esters.

Additional Components

The composition of the present invention may include other additional components, which may be selected by the artisan according to the desired characteristics of the final product and which are suitable for rendering the composition more cosmetically or aesthetically acceptable or to provide them with additional usage benefits. Such other additional components generally are used individually at levels of from about 0.001% to about 10%, preferably up to about 5% by weight of the composition.

A wide variety of other additional components can be formulated into the present compositions. These include: other conditioning agents such as hydrolysed collagen with tradename Peptein 2000 available from Hormel, vitamin E with tradename Emix-d available from Eisai, panthenol available from Roche, panthenyl ethyl ether available from Roche, hydrolysed keratin, proteins, plant extracts, and nutrients; preservatives such as benzyl alcohol, methyl paraben, propyl paraben and imidazolidinyl urea; pH adjusting agents, such as citric acid, sodium citrate, succinic acid, phosphoric acid, sodium hydroxide, sodium carbonate; coloring agents, such as any of the FD&C or D&C dyes; perfumes; ultraviolet and infrared screening and absorbing agents such as benzophenones; and antidandruff agents such as zinc pyrithione; non-ionic surfactant such as mono-9-octadecanoate poly(oxy-1,2-ethanediyl) supplied as, for example, Tween 20; and buffer such as aminomethyl propanol.

Product Forms

The compositions of the present invention can be in the form of rinse-off products or leave-on products, and can be formulated in a wide variety of product forms, including but not limited to creams, gels, emulsions, mousses and sprays. The composition of the present invention is especially suitable for hair conditioners especially leave-on, leave-in, and/or no-rinse hair conditioners. Leave-on and leave-in hair conditioners are generally used on dry, semi-wet, and/or wet hair without rinsing out the conditioner. By no-rinse hair conditioners, what is meant herein is a hair conditioner used on semi-wet to wet hair after shampooing, without rinsing out the conditioner, preferably inside of bathroom.

Key Features of the Invention

The present invention is directed to the following key features.

1. A hair conditioning composition comprising by weight: from about 1.0% to about 10% of a cationic surfactant; from about 2.5% to about 30% of a high melting point fatty compound; from about 0.2% to about 10% of a cyclic compound selected from the group consisting of a vitamin B3 compound, a xanthine compound, a salicylic acid ester, and mixtures thereof; from about 0.1% to about 15% of a compound having at least three large head groups; and an aqueous carrier.

2. The hair conditioning composition of Claim 1 wherein the vitamin B3 compound is niacinamide, a xanthine compound is caffeine, a salicylic acid ester is ethylhexyl salicylate.

3. The hair conditioning composition of any of the preceding claims wherein the at least three large head groups are at least three hydrocarbon groups wherein each of the hydrocarbon groups has from about 5 to about 50 carbons.

4. The hair conditioning composition of any of the preceding claims, wherein the compound having at least three head groups are triester having three hydrocarbon groups wherein each of the hydrocarbon groups has from about 5 to about 50 carbons.

5. The hair conditioning composition of any of the preceding claims, wherein the compound having at least three head groups are glycerol triester having three hydrocarbon groups wherein each of the hydrocarbon groups has from about 5 to about 50 carbons.

6. The hair conditioning composition of any of the Claims 1-3, wherein the compound having at least three head groups are alkyl glutamate diesters having three hydrocarbon groups wherein each of the hydrocarbon groups has from about 5 to about 50 carbons.

7. The hair conditioning composition of any of the preceding claims, wherein the composition comprises from about 0.6% to about 3% of the cyclic compound.

8. The hair conditioning composition of any of the preceding claims, wherein the composition comprises from about 0.5% to about 5% of a compound having at least three large head groups.

9. The hair conditioning composition of any of the preceding claims, wherein the weight ratio of the cyclic compounds to the compound having at least three large head groups is from about 0.3:1 to about 2.2:1.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

| | |
|---|---|
| Ratio of silicone blocks:alkylene oxide blocks | 1:1 |
| Total Viscosity | 4700 mPa · s |

Method of Preparation

The above hair care compositions of "Ex. 1" through "Ex. 5" of the present invention and hair care compositions of "CEx. i" through "CEx. ii" as comparative examples can be prepared by any conventional method well known in the art.

Properties and Conditioning Benefits

For some of the above compositions, properties and conditioning benefits are evaluated by the following methods. Results of the evaluation are also shown above.

The embodiments disclosed and represented by "Ex. 1" through "Ex. 5" are hair conditioning compositions of the present invention which are particularly useful for the use on semi-wet to wet hair after shampooing, without rinsing out the conditioning composition. Such embodiments have many advantages. For example, they provide improved hair manageability such as reduced hair volume. Such advantages can be understood by the comparison between the example of the present invention "Ex. 1" and the comparative examples "CEx.i and CEx.ii".

Compositions (wt %)

| Components | | Ex.1 | Ex. 2 | Ex. 3 | Ex. 4 | Ex. 5 | CEx. i | CEx. ii |
|---|---|---|---|---|---|---|---|---|
| Behenyl trimethylammonium methosulfate | | 2.97 | 2.97 | 2.97 | 2.97 | 2.97 | 2.97 | 2.97 |
| Cetyl alcohol | | 1.18 | 1.18 | 1.18 | 1.18 | 1.18 | 1.18 | 1.18 |
| Stearyl alcohol | | 2.93 | 2.93 | 2.93 | 2.93 | 2.93 | 2.93 | 2.93 |
| Cyclic compound | Niacinamide | 1.8 | 2.5 | 1 | — | — | 2.5 | — |
| | Ethylhexyl salicylate | — | — | — | — | 2 | — | — |
| | Caffeine | — | — | — | 1 | — | — | — |
| Compound having at least three large head groups | Trioctanoin | 1.8 | 1.8 | 2 | 1 | — | — | 1.8 |
| | Phytosteryl/ Octyldodecyl Lauroyl Glutamate *1 | — | — | — | — | 2 | — | — |
| | Caprylic/capric triglyceride | 0.8 | — | — | — | — | — | — |
| Silicone compound *2 | | 2.5 | 2.5 | 2.5 | 2.5 | 2.5 | 3 | 3 |
| Preservatives | | 0.5 | 0.5 | 0.5 | 0.5 | 0.5 | 0.5 | 0.5 |
| Perfume | | 0.5 | 0.5 | 0.5 | 0.5 | 0.5 | 0.5 | 0.5 |
| Panthenol | | — | — | — | — | 0.005 | — | — |
| Panthenyl ethyl ether | | — | — | — | — | 0.005 | — | — |
| Deionized Water | | q.s. to 100% of the composition | | | | | | |
| Preparation of hair switch | | NR | NR | NR | NR | NR | NR | NR |
| Volume (mm$^2$) | | 102,600 | — | — | — | — | 288,340 | 251,816 |

Definitions of Components

*1 Supplied with a tradename ELDEW PS-203

*2 Silicone compound: Available from Momentive having the following formula: M-Y-[-(N$^+$R$_2$-T-N$^+$R$_2$)-Y-]$_m$-[-(N$^+$R$^2_2$-A-E-A'-N$^+$R$^2_2$)-Y-]$_k$-M

| | |
|---|---|
| M | lauric ester |
| Y | K—S—K |
| K | CH$_2$—CHOH—CH$_2$—O—C$_3$H$_6$ |
| S | PDMS block with 368 siloxane units |
| R, R$^2$ | Methyl |
| T | C$_6$H$_{12}$ |
| A | CH$_2$—COO— |
| A' | CO—CH$_2$ |
| E | Ethylene oxide (CH$_2$—CH$_2$—O) with average degree of ethoxylation of 2 |

Hair Volume (i) Preparation of Hair Switch

For the volume measurement, 15 gram hair switch with a length of 10 inch are used. The hair switches are prepared by following steps:

(1) The hair switches are bleached and combed in the same way. Then, applying 1.5 cc of non-conditioning shampoo per one hair switch, lathering, rinsing and drying the hair switches;

(2) Applying a non-conditioning shampoo at a level of 1.5 cc per one hair switch and lathering the hair switch; and rinsing the hair switch; and (3) Applying conditioner at a level of 1.5 cc per one hair switch and treating the hair switch; and (4) not-rinsing the hair switch (described as "NR") or rinsing the hair switch (described as "R"); and
(5) Then drying the hair switch at 50° C. and in low humidity (30%) environment for 1.5 h;
(6) Then placing the hair switches in a high humidity (75%) environment, for 1 h at 28° C., in which the hair switches tend to expand and increase the volume.

Hair switches are ready for volume measurements.

(ii) Volume Measurements

Volume are measured by a method described in Canadian patent application publication No. CA2567712 A1. In more detail, the volume (mm3) is measured by conducting 3D reading by the laser scanning device.

(iii) Evaluation

The above measurement in the step (ii) are conducted on at least 3 different hair switches prepared by the step (i) per one conditioner, and then calculate an average of the volume.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention

What is claimed is:

1. A hair conditioning composition comprising by weight:
   from about 1.0% to about 10% of a cationic surfactant;
   from about 2.5% to about 10% of a high melting point fatty compound selected from the group consisting of cetyl alcohol, stearyl alcohol, and combinations thereof;
   from about 0.2% to about 10% of niacinamide;
   from about 0.5% to about 5% of a triester having three hydrocarbon groups wherein each of the hydrocarbon groups has from about 5 to about 35 carbons selected from the group consisting of trioctanoin, caprylic/capric triglycerides, and combinations thereof; and
   an aqueous carrier.

2. The hair conditioning composition of claim 1 wherein the composition comprises from about 0.6% to about 3% of the niacinamide.

3. The hair conditioning composition of claim 1 wherein the weight ratio of the niacinamide to the triester having three hydrocarbon groups is from about 0.3:1 to about 2.2:1.

* * * * *